US00PP20279P2

(12) United States Plant Patent
Merritt

(10) Patent No.: US PP20,279 P2
(45) Date of Patent: Sep. 8, 2009

(54) LILY PLANT NAMED 'BJM 001'

(50) Latin Name: *Lilium longiflorum*
Varietal Denomination: BJM 001

(75) Inventor: Richard H. Merritt, Bridgewater, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 12/148,732

(22) Filed: Apr. 21, 2008

(51) Int. Cl.
*A01H 5/00* (2006.01)

(52) U.S. Cl. ..... Plt./313
(58) Field of Classification Search ..... Plt./313
See application file for complete search history.

*Primary Examiner*—Kent L Bell
(74) *Attorney, Agent, or Firm*—Klarquist Sparkman, LLP

(57) ABSTRACT

A new lily variety distinguished by (1) stem thickness supported by flower crown without bending (1.5 cm in diameter); (2) straight stems with even leaf distribution from bottom to top (more than 100 leaves per plant); (3) flower crown compact (around 36 cm); (4) flower sizes larger (16 cm long 7–9 cm wide at open stage); (5) continuous blooms for two to four weeks; (6) coloration of leaves uniform from bottom to top; (7) height of plant around 30 cm; and (8) snowy white flowers.

1 Drawing Sheet

Latin name of the genus and species of the plant claimed: *Lilium longiflorum.*

Variety denomination: 'BJM 001'.

FIELD

The present invention comprises a new and distinct cultivar of *Lilium longiflorum* named 'BJM 001' characterized by numerous large snowy white compact trumpet flower crowns on strong stems with rich green foliage. This cultivar was originally bred as an Easter Lily pot plant, but unlike current commercial cultivars, this cultivar is winter hardy, sprouts freely and can provide a garden/specimen plant of up to 50 blooms.

SUMMARY

A new and distinct cultivar of *L. longiflorum* plant named 'BJM 001' substantially as herein shown and described in FIG. 1. The parentage of the new variety is not known. The variety was developed as part of a breeding program in New Brunswick, N.J., as was identified in 1995 as one of seven seedling lines. Of the seven lines, 10 specimens were collected from five of the seven lines. DNA fingerprinting analysis indicates that the new variety does not match any of the germplasm tested from a commercial source.

The new variety is characterized by numerous large snowy white compact trumpet flower crowns on short straight strong stems with rich green plentiful foliage. The following traits have been repeatedly observed in asexually propagated progeny and are determined to be the basic characteristics of this invention which in combination distinguish this lily as a new and distinct cultivar: (1) stem thickness supported by flower crown without bending (1.5 cm in diameter); (2) straight stems with even leaf distribution from bottom to top (more than 100 leaves per plant); (3) flower crown compact (around 36 cm); (4) flower sizes larger (16 cm long and 28 cm wide at open stage); (5) continuous blooms for two to four weeks; (6) coloration of leaves uniform from bottom to top; (7) height of plant around 30 cm; and (8) snowy white flowers. To the inventor's knowledge, there are no other cultivars of lily of this size of plant or in terms of the superior plant and flower quality in the market.

'BJM 001' has been asexually reproduced by tissue culture in New Brunswick, N.J. No evidence of off-types of 'BJM 001' have been observed or reported to us. Thus, it is concluded that 'BJM 001' is stable and reproduces true to type in successive generations of asexual reproduction.

The following detailed description concerns the variety 'BJM 001'. Progeny of the original plant have been observed growing in cultivated areas in New Brunswick, N.J. Certain characteristics of this variety, such as growth and color, may change with changing environmental conditions (such as light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart or the Munsell color system.

Figure 1:
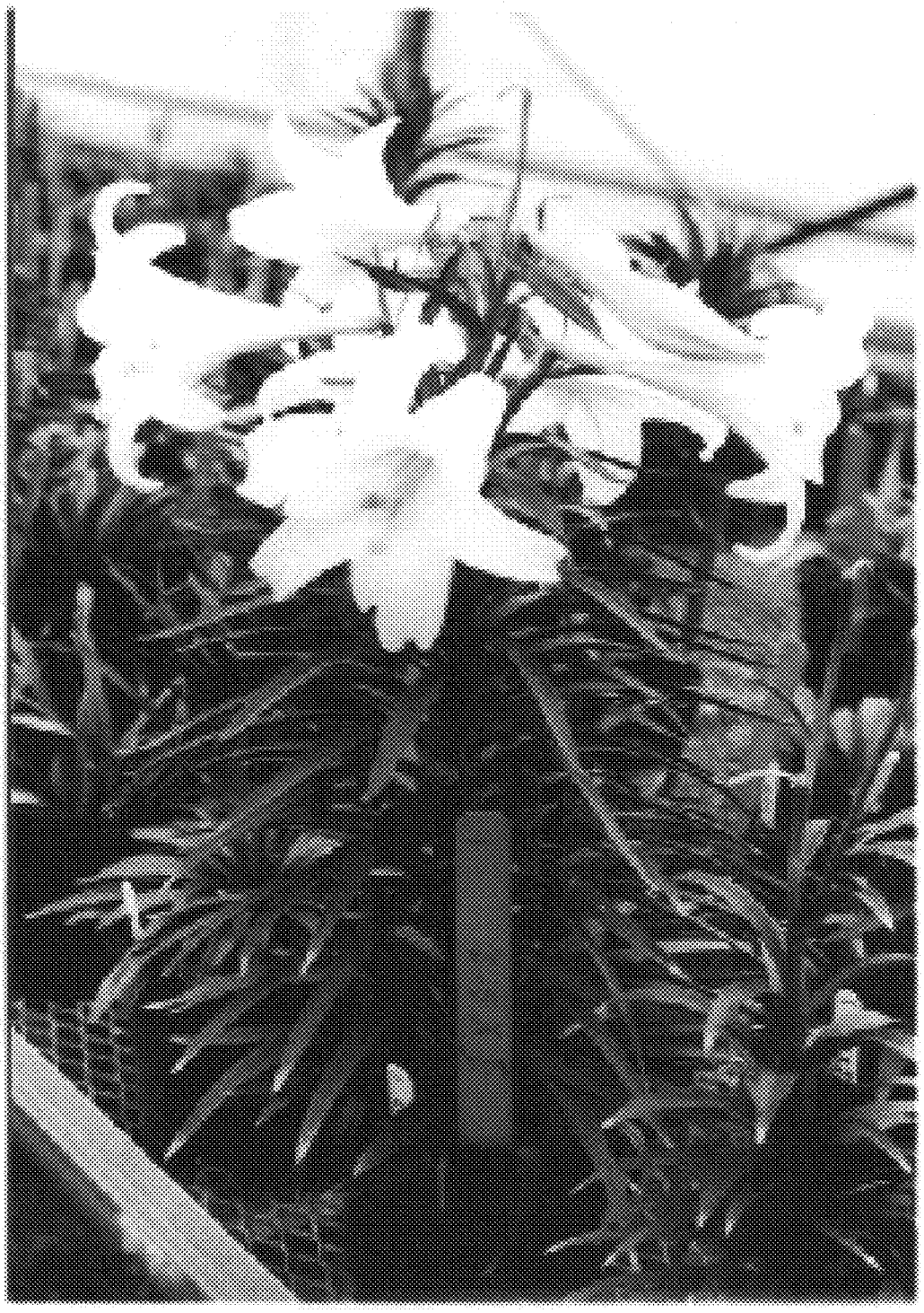
FIG. 1 is a photograph showing the new variety.

The colors of an illustration of this type may vary with lighting and other conditions under which conditions and, therefore, color characteristics of this new variety should be determined with reference to the observations described herein, rather than from this illustration alone.

DETAILED BOTANICAL DESCRIPTION

The following description of variety 'BJM 001' is based on progeny produced under asexual reproduction by tissue culturing. The plant was two-years old and was observed growing in New Brunswick, N.J.

Plant:

*Origin.*—New Brunswick, N.J.
*Parentage.*—*Lilium longiflorum.*
*Seed parent.*—*Lilium longiflorum* selection.
*Commercial classification.*—Bedding/specimen plant.

*Classification.*—Division 5, according to the Horticultural Classification of Lilies by The Royal Horticultural Society of London.

*Height.*—Approximately 30 cm. from the top of the soil to the top of the flowers from bulbs of 11.3 cm in circumference.

*Stem color.*—Green (Munsell 7.5GY V6/C6).

*Stem diameter.*—12–16 cm.

*Growth habit.*—Upright, strict.

*Foliage.*—Predominantly cauline.

*Leaf arrangement.*—Alternate.

*Leaf size.*—Approximately 11 cm long and 1.8 cm wide; edge is smooth (not serrated).

*Leaf shape.*—Linear—lanceolate.

*Texture.*—Shining and glabrous.

*Color.*—Green Munsell 7.5GY V4/C4 top, 5GY V4/C6 bottom.

*Bulbs.*—Globose with prominent scales and lobes.

*Size.*—Variable, ranging to approximately 15.5 cm in circumference as used commercially.

*Color.*—White (RHS 155B).

The bud:

*Size.*—6 cm long and 18 mm wide just prior to opening.

*Shape.*—Ellipsoidal, sulcate with 3 grooves.

*Rate of opening.*—Approximately 6.5 cm/day depending on temp.

*Color.*—Light yellow or light greenish-yellow (Munsell 2.5GY V8/C8–10).

The flower:

*Blooming habit.*—Terminal inflorescence with 1–4 perpendicularly angled flowers.

*Days to bloom.*—Flowers approximately 100 days (with photoperiodic light) and 120 days (natural days) after spring greenhouse planting under typical commercial flower forcing conditions of 15.5 Celsius night time temperatures.

*Inflorescence size.*—Approximately 15 cm high and 28 cm wide when there are 3 flowers present.

*Flower size.*—Large.

*Diameter.*—Approximately 15 cm.

*Depth.*—Approximately 12.5 cm.

*Borne.*—In an umbel or modified raceme of 1–4 flowers from bulbs 11.3 cm in circumference.

*Shape.*—Funnelform.

*Tepals.*—Both surfaces inner and outer are white (RHS 155B), reflexed; margins are not separated.

*Tepal number.*—6.

*Arrangement.*—Alternate.

*Tepal shape.*—Ovate or oblanceolate with obtuse apex.

*Texture.*—Shining and glabrous.

*Size.*—Length: approximately 6 cm. Width: inner tepals — approximately 50 mm. Outer tepals — approximately 38 mm. Length of Imbrication of tepals: approximately 60 mm.

*Nectary.*—Description: obscure nectary.

*Projections.*—Absent.

*Spots.*—Absent.

*Blush.*—Absent.

*Color.*—White (RHS 155B).

*Bottomside.*—White (RHS 155B) to light green (Munsell 7.5GY 8V/2C) basally.

*Fragrance.*—Absent.

*Pedicel.*—All terminal, glabrous.

*Length.*—Approximately 5 cm long and 5 mm wide.

*Color.*—Dark green (Munsell 7.5GY V6/C6).

*Orientation.*—Ascending upwardly at an angle approximately 45° from the horizontal.

The reproductive organs:

*Stamens.*—Slightly exserted.

*Number.*—6.

*Anthers before dehiscence.*—Approximately 6 mm long×2 mm wide. Color: yellow (Munsell 2.5Y V7/C10).

*Filaments.*—Length: approximately 5 cm; Color: light green (Munsell 2.5GY V/C10).

*Pollen.*—Color: yellow (Munsell 2.5GY V8/C10).

*Pistil.*—Exserted beyond stamens.

*Number.*—1 (compound ovary with 3 fused carpels).

*Style.*—Length: approximately 19 mm; Color: light green (Munsell 2.5GY V8/C2).

*Stigma.*—Color: light green, slightly pinkish (Munsell 2.5GY V7/C8).

The fruit: Fertility: absent; no fruit formed.

DNA fingerprint: The fingerprinting method used was RAPDs (random amplified polymorphic DNA). The fragments generated using RAPDs were separated on acrylamide gels and silver stained. A total of three primers were used. These primers yielded eleven useful markers. The data were analyzed using NT-SYS pc (Applied Biostatistics).

| Primer | A6 | A6 | A6 | A12 | A17 | A17 |
|---|---|---|---|---|---|---|
| Size | 500 | 900 | 1000 | 600 | 400 | 550 |
| 6-2 | 1 | 1 | 1 | 0 | 0 | 1 |

| Primer | A17 | A17 | B2 | B2 | B2 |
|---|---|---|---|---|---|
| Size | 790 | 880 | 250 | 310 | 440 |
| 6-2 | 1 | 1 | 1 | 1 | 1 |

I claim:

1. A new and distinct variety of lily plant, substantially as herein shown and described.

* * * * *